United States Patent [19]

Gans et al.

[11] Patent Number: 5,336,692
[45] Date of Patent: Aug. 9, 1994

[54] OINTMENT BASE AND METHOD OF USE

[75] Inventors: Eugene H. Gans, Westport, Conn.; Hans R. Süess, Starrkirch, Switzerland

[73] Assignee: Medicis Pharmaceutical Corporation, New York, N.Y.

[21] Appl. No.: 714,311

[22] Filed: Jun. 18, 1991

Related U.S. Application Data

[63] Continuation-in-part of Ser. No. 545,940, Jun. 28, 1990, abandoned.

[51] Int. Cl.$^5$ .................. A61K 47/00; A61K 31/01; A61K 31/695; A61K 7/42
[52] U.S. Cl. ......................... 514/772; 424/59; 514/63; 514/724; 514/726; 514/785; 514/787; 514/969
[58] Field of Search ............... 514/63, 724, 772, 969, 514/785, 787, 726; 424/59

[56] References Cited

U.S. PATENT DOCUMENTS

| | | | |
|---|---|---|---|
| 2,988,473 | 6/1961 | Mallis et al. | 514/63 |
| 4,355,046 | 10/1982 | Süess | 514/772 |
| 4,532,132 | 7/1985 | Keil | 514/772 |

OTHER PUBLICATIONS

Kuwata, Satoshi, "Cyclosiloxane-containing cream compositions," Essential Oils, Cosmetics, 110:12115m (1989).

*Primary Examiner*—Marianne M. Cintins
*Assistant Examiner*—K. Weddington
*Attorney, Agent, or Firm*—Jones & Askew

[57] ABSTRACT

High molecular weight petroleum fractions which have a low white oil content are admixed with a volatile siloxane, hexamethyldisiloxane, octamethylcyclotetrasiloxane and/or decamethylcyclopentasiloxane and a compound that is both hydrophobic and hydrophilic to provide an ointment base which enables these petrolatum fractions to be spread easily on the skin. Evaporation of the solvent leaves a high molecular weight petrolatum film on the skin that is nonirritating and yet highly resistant to mechanical removal.

42 Claims, No Drawings

OINTMENT BASE AND METHOD OF USE

CROSS-REFERENCE TO RELATED APPLICATIONS

This is a continuation-in-part of U.S. patent application Ser. No. 07/545,940, filed on Jun. 28, 1990 now abandoned.

TECHNICAL FIELD

The present invention comprises a composition for the application of high molecular weight petroleum fractions onto a surface. More particularly, the present invention comprises a composition which is an admixture of high molecular weight petroleum fractions and hydrophobic/hydrophilic solvents so that the resulting admixture can be easily applied to a surface, such as skin, hair, nails, leather, plant surfaces, wood, plastics, and metals.

BACKGROUND OF THE INVENTION

The term "emulsion" as used herein means either a lotion that is liquid or semi-liquid or a gel.

The skin is the largest organ in the human body. It serves primarily as protection of the body against the environment. The skin is constantly exposed to the damaging effects of ultraviolet radiation, chemicals, and surroundings that are either too dry or too moist.

Protection against ultraviolet radiation can be provided by avoiding exposure to sunlight and/or using creams or other preparations providing protection from the sun. The skin protects itself by producing sebum (tallow) by the sebaceous glands and, to a much smaller extent, by the fat formed through the keratinization of the cells. The activity of the sebaceous glands is controlled by hormones and is reduced with age. Consequently, the fat supply of the skin is often insufficient in older people.

Skin fat is partially removed by hygienic procedures, such as washing, bathing or showering, particularly those portions that are most frequently washed, such as hands and face. In the case of low humidity, as in extreme cold, the unprotected skin suffers loss of moisture. The skin dries out and painful skin cracks can result. On the other hand, prolonged contact with water, particularly when the water's surface tension is strongly reduced by soap or synthetic detergents, causes skin damage through maceration.

The cosmetics industry has sought to relieve drying out of the skin through so-called moisturizers. These moisturizers generally are an oil-in-water emulsion, a water-in-oil emulsion, or mixed emulsions. They contain emulsifiers which facilitate the penetration of water and the removal of the dried-out fat film by washing. These preparations only partially limit trans epidermal water loss of the skin. The moisture retention of the skin is therefore unsatisfactory.

Petrolatum, on the other hand, can, to a great extent, limit the water loss of the skin (see, e.g., "Cosmetics and Toiletries" 93, pg. 27 (1978)). However, this effect is not totally one of reduction of the trans epidermal water loss by occlusion, but rather is based upon a pharmacological effect of the petrolatum grease on the skin. Petrolatum grease, however, is most unsatisfactory from a cosmetic standpoint because of its high viscosity. It penetrates poorly into the skin and adheres to it insufficiently, so that it is easily removed mechanically and by washing. Furthermore, it may be applied only with difficulty because of its high viscosity, so that an unpleasant greasy and sticky layer is formed.

It is known that certain petrolatums can irritate the skin and can also produce acanthosis of the epidermis. The properties mentioned come mainly from the components of petrolatum boiling below 180° C. at 2 mbar (see, e.g., Schaaf, "Probleme der dermatologischen Grundlagenforschung," pg. 105 (1969)). The low-irritation fraction, because of its high viscosity, is only poorly capable of being distributed over the skin and is, consequently, cosmetically unsatisfactory.

In contrast, the petrolatum fractions utilized in accordance with the present invention, from which the more volatile oils (known to those of ordinary skill in the art as "white oils") have to a large extent been separated, have been found non-irritating to the skin.

Little pharmaceutical, cosmetic, veterinary or horticultural attention has been paid to the application of petrolatum fractions that exceed liquid petrolatum and petrolatum in molecular weight, viscosity and melting point. The higher molecular weight, higher viscosity, higher melting point fractions from that of higher viscosity Petrolatum, U.S.P. grades to highly viscous semi-solids and solids are very difficult, uncomfortable and anesthetic in application. In addition, they do not have the intrinsic ability to significantly contact the pores or surface layers of the substrates to which they are being applied. The addition of these highly viscous petrolatum fractions results in greasy or oily residues that can attract dirt and other pollutants. The addition of conventional solvents, such as mineral spirits, results in solutions that are unacceptable or unsafe for human, animal or horticultural use.

U.S. Pat. No. 4,355,046, to Süess, which is incorporated herein by reference, discloses admixing the high molecular weight petroleum fractions with certain volatile siloxanes, preferably octamethylcyclotetrasiloxane, decamethylcyclopentasiloxane and/or hexamethyldisiloxane.

The composition disclosed in the '046 patent is an admixture of approximately 10% to 90% by weight of high molecular weight petroleum fractions in which the white oil content does not exceed approximately 20% and approximately 90% to 10% by weight of octamethylcyclotetrasiloxane, decamethylcyclopentasiloxane and/or hexamethyldisiloxane.

The compositions that are disclosed in the '046 patent are highly hydrophobic, not dispersible or soluble in water and are very viscous. Thus, the user needs to exert more than usual application energy to rub them into the substrate.

What is needed is a composition that contains the beneficial high molecular weight petroleum fractions and, at the same time, is easy to apply to a surface. Such a composition would have wide acceptance. In addition, the trans epidermal moisture loss would be reduced, thereby assuring natural moisturization of the drier horny layer of the skin.

SUMMARY OF THE INVENTION

As will be seen, the present invention overcomes these and other problems associated with prior art methods of providing an effective ointment base. By admixing the high molecular weight petroleum fractions, siloxane compounds, and compounds that have certain hydrophobic and hydrophilic properties, the adherence of the high molecular weight petroleum fractions on a surface can be increased substantially without the need for excessive application energy.

The hydrophobic/hydrophilic compounds that are contemplated as part of the present invention typically have a hydrophobic portion in the molecule and a hydrophilic portion in the molecule. For example, an aliphatic alcohol will have a hydrophobic portion of the molecule that is typically made up of carbon atoms and a hydrophilic portion of the molecule that is a water-loving hydroxyl group.

The ointment base of the present invention is provided for cosmetic or medication application to healthy, injured or diseased skin. In addition, the ointment base that comprises the present invention can be applied to other surfaces including, but not limited to, leather, plant surfaces, wood, plastics and metals.

Accordingly, it is an object of the present invention to provide an improved ointment base with a high molecular weight petroleum fraction that is easy to apply to the surface and strongly adheres to the surface.

It is yet another object of the present invention to provide an improved ointment base that significantly improves epidermal moisture retention by enhancing moisture uptake and reducing excessive trans epidermal moisture loss.

It is another object of the present invention to provide an improved ointment base that can be used as a carrier for a pharmaceutically active agent.

It is another object of the present invention to provide an improved ointment base that can be used as a skin moisturizer and skin protectant.

It is an object of the present invention to provide an ointment base capable of being well distributed on the skin and on other substrates and adhering well to them.

It is an object of the present invention to provide an ointment base that would be free of irritation and will provide protection of long duration even after frequent washing.

It is yet another object of the present invention to provide an improved ointment base which can be applied to damaged or diseased skin to reduce irritation.

It is another object of the present invention to provide an ointment base that is suitable as a base for cosmetics.

It is another object of the present invention to provide an ointment base that is suitable for use as a base for dermatologic applications and applications to other surfaces.

These and other objects, features and advantages of the present invention will become apparent after a review of the following detailed description of the disclosed embodiments and the appended claims.

DETAILED DESCRIPTION OF THE INVENTION

It has been found that the disadvantages of the previously known preparations can be avoided if the high molecular weight petroleum fraction and the siloxane admixture are further admixed with between approximately 0.25% and 10% of selected compounds that have certain hydrophobic/hydrophilic properties. It is to be understood that these percentages are of the final product with diluents such as water.

The present invention comprises an ointment base for use on a surface, in which at least 10 percent by weight thereof is composed of an admixture comprising 5 to 90 percent by weight of petrolatum fractions. The petrolatum fractions in which the ratio by weight of solid constituents to constituents that are liquid at 20° to 50° C. in petrolatum fraction is greater than 3:1. In the admixture, approximately 4 to 40 percent by weight of a material serving as a solvent for the petrolatum fractions; and between approximately 0.3% and 15% by weight of a material that is both hydrophobic and hydrophilic.

Examples of these hydrophobic/hydrophilic compounds are aromatic, aliphatic, and silanyl alcohols. Other compounds that can be used according to the present invention include aldehydes, esters and ketones. Specific examples of the aromatic compounds that can be used according to the present invention are benzyl alcohol, benzaldehyde, phenylethyl alcohol, benzyl glycolate and benzophenone. Aliphatic compounds that can be used according to the present invention include octanol, dodecanol, and ethyl lactate. The aliphatic compounds preferably contain at least 7 carbon atoms and can be straight chained or branched. The silanyls that can be used according to the present invention include silanyl aldehydes, silanyl esters, and silanyl ketones.

The admixing of the above-given quantities of hydrophobic/hydrophilic compounds with the high molecular weight petroleum fractions is preferably carried out at a slightly raised temperature. Upon cooling, a composition results that is easily applied onto a surface.

The preferred ratios within the ranges of composition given above are from 3% to 90% by weight of the high molecular weight petroleum fractions to a 95% to 10% by weight of siloxane solvent. The preferred range of high molecular weight petroleum fractions is between approximately 8% and 70%. The concentration of the high molecular weight petroleum fraction in the present invention will depend largely upon the desired physical form of the final product. If the final ointment is to be a liquid or semi-liquid, the preferred concentration of the high molecular weight petroleum fraction will be between approximately 3% and 10%. If the final ointment is to be a lipid gel, the preferred concentration of high molecular weight petroleum fraction will be between approximately 40% and 90%. The preferred concentration of siloxane is between approximately 5% and 80% with the most preferred concentration of siloxane being between approximately 8% and with 60%. The preferred siloxanes include, but are not limited to, octamethylcyclotetrasiloxane, decamethylcyclopentasiloxane and/or hexamethyldisiloxane. Thus, the ointment base preferably has a ratio by weight of the petrolatum fractions to the solvent material in the range of from approximately 15:70 to 70:20.

Preferably, according to the present invention, a petrolatum fraction is used in which the weight ratio of solid to liquid components at 20° to 25° C. is greater than 3:1 and, more preferably, lies within the range of from 4 to 100 or higher. According to a particularly preferred embodiment, high melting microcrystalline waxes are contained in the ointment base, preferable to the extent of 3 to 15 percent by weight of the petrolatum and siloxane solvent.

The high molecular weight petroleum fraction component of the ointment base according to the invention comprises high molecular weight petroleum fractions that are physiologically tolerable in which little or no white oil remains. More particularly, the white oil content should be under approximately 20% by weight. The white oils include the low-boiling, low-viscosity components of the petrolatum. These low-boiling, low-viscosity components are known to be irritating to the skin. After the separation of the white oil, for example, by distillation, an irritation-free high molecular weight petrolatum fraction is obtained. Preferably, the petrolatum fraction contains a minimum of molecules having fewer than approximately 20 carbon atoms.

It is particularly useful to utilize those petrolatum fractions that have a weight ratio of solid to liquid components of above 3 at a temperature from 20° to 25° C. However, the ratio of solid material to materials that are liquid from between 20° to 25° C. should not exceed 40 to 100.

As mentioned hereinabove, the ointment bases according to the invention contain hydrophobic/hydrophilic compounds. These hydrophobic/hydrophilic compounds are physiologically compatible and can be warmed above the melting range of the petrolatum fraction without degradation. Furthermore, many of the preferred hydrophobic/hydrophilic compounds are volatile. It is to be understood that the hydrophobic/hydrophilic compounds, because of their lower heat of evaporation, may evaporate off the skin. The hydrophobic/hydrophilic compounds can be used individually or in mixtures thereof.

According to the preferred embodiment of the invention, there is used as petrolatum component a petrolatum of which the liquid components are greatly reduced in proportion to the solid components. In this manner, a still better skin protection is obtained, because these preparations provide a durable skin protection even under the effect of detergents. Commercial grades of petrolatum sold under generic names, trademarks and U.S.P. names that meet pharmacopeia requirements consist of about equal parts of materials that are liquid at 20° to 25° C. and solid materials melting above 60° C. If a greater ratio of solid to liquid parts, i.e., above 3:1 and preferably in the range from approximately 4 to 100, is selected, highly viscous compositions that are difficult to spread on the skin are obtained.

By admixing octamethylcyclotetrasiloxane, decamethylcyclopentasiloxane and/or hexamethyldisiloxane with the high molecular weight petroleum fractions, the resulting composition is more easily spread and adheres strongly to surfaces. The combination of 8 to 50 percent by weight of the siloxane with 92 to 60 percent by weight of the high molecular weight petroleum fractions having a weight ratio of solid to liquid components of 4 to 100 is particularly favorable. According to the present invention, the siloxane/petroleum admixture can be greatly improved by the addition of hydrophobic/hydrophilic compounds at a concentration of between approximately 0.3% and 10% by weight. The preferred concentration range is between approximately 0.5% and 2.5%. The preferred hydrophobic/hydrophilic compounds are benzyl alcohol, phenylethyl alcohol, octanol or mixtures thereof.

Any unctuous luster remaining on the skin by the use of this preparation can be avoided in practice by increasing the proportion of high-melting components of the petroleum by the addition of high-melting microcrystalline waxes without thereby impairing the good spreading capabilities of the composition. High-melting microcrystalline waxes with a melting region in the range from 85° to 95° C. provide good results. The addition of high-melting crystalline waxes (Fp about 90° C.) in a proportion of approximately 5 to 15 percent by weight of the petrolatum fraction and the hydrophobic/hydrophilic compounds, provides white opaque compositions which adhere well when spread on the skin and leave very little luster or shine.

It may be advantageous to add still other physiologically compatible additives, particularly in small quantities, e.g., less than approximately 10 percent. It is preferred, in some cases, to add physiologically compatible lower alcohols, as, for example, ethyl and isopropyl alcohols. In the manufacture of the dermatologic or cosmetic base of the present invention, small quantities of such additives can be introduced to produce preparations suitable for cosmetics.

Still other conventional additives can be added to the preparations according to the invention, so long as they are physiologically tolerable and harmless and are compatible with the essential components of the composition. Examples of such additives are ultraviolet absorbers, perfumes and thickening media, as, for example, ceresin, ozokerite, aluminum stearate, polyvinyl stearate and derivatives of polyvinyl pyrrolidone. For modification of skin "feel", isopropyl and glyceryl esters of fatty acids, such as isopropyl and glyceryl myristate, and lanolin derivatives can be added.

The preparations made up of the high molecular weight petroleum fractions, the specified octamethylcyclotetrasiloxane, decamethylcyclopentasiloxane and/or hexamethyldisiloxane and the hydrophobic/hydrophilic compounds in the above-mentioned quantity ratios are good ointment bases and skin care and skin protection preparations that are easily spread on the skin and penetrate also into the deeper part of the horny layer of the skin. After evaporation of the solvent, a hydrocarbon mixture remains which no longer can be fully removed even by repeated washing of the skin with soap or synthetic detergents.

Skin thus protected provides resistance to the passage of water in both directions and likewise to the penetration of water soluble noxious substances. The high molecular weight petroleum fractions are not readily saponifiable. Noxious chemical substances are present mostly in aqueous solutions, often at higher values of pH and/or in the presence of wetting agents, such as household washing materials or cold waving preparations. Thus, the ointment base, according to the present invention, develops a protective layer on the skin.

Because the compositions according to the invention need no sensitizing or allergenic preservatives, they tend to be non-allergenic. The ointment base according to the present invention is practically an odorless composition. Thus, allergic and phototoxic phenomena that can occur with the use of scents and the like can be avoided. This is particularly important when preparations made in accordance with the invention to which suitable ultraviolet absorbers had been added are intended to serve as protection from solar radiation.

For this purpose, the compositions according to the present invention are particularly advantageous because the petrolatum in itself already has good sun-protection properties and because the emulsifier-free and rinsible emulsifier-free preparation is not washed away in bathing and is less easily worn away mechanically by sand. Light-protection preparations that are effective for a long time are thus obtained, which is important from the standpoint of protection of the skin from light.

The freedom from odor of hand protection preparations is particularly a requirement when the hands thereafter come into contact with food since the possibility of an undesired odor transmission exists in the case of scented products. The preparations according to the invention, including their resistance to loss due to washing, moisture and abrasion are therefore particularly well suited as occupational protection creams.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

The formulations in Examples 1 and 2 are gels that can be applied directly or adapted to an aerosol or pump applicator if desired. In addition, the following formulation can be easily spread on a surface such as skin.

| | |
|---|---|
| Special Petrolatum Fraction | 60.0 |
| Benzyl Alcohol | 2.0 |
| Cyclomethicone | 37.5 |
| Propellant (optional) | Q.S. |

The concentration of all components is expressed as percent by weight. The components are warmed until a clear solution is produced, after which the composition is cooled to room temperature while stirring.

EXAMPLE 2

| | |
|---|---|
| Special Petrolatum Fraction | 58 |
| Benzyl Alcohol | 1.5 |
| Octanol | 0.5 |
| Phenylethyl alcohol | 1.0 |
| Cyclomethicone | 39.0 |

The concentration of all components is expressed as percent by weight. The components are warmed until a clear solution is produced, after which the composition is cooled to room temperature while stirring.

EXAMPLE 3

The formulations in Examples 3 through 5 are water-in-oil emulsions which can be applied directly or by aerosol pump and spray.

| | |
|---|---|
| Special Petrolatum Fraction | 6.0 |
| Benzyl Alcohol | 1.0 |
| Octanol | 0.2 |
| Cyclomethicone | 10.0 |
| Dimethicone copolyol | 10.0 |
| Sorbitan laurate | 1.0 |
| Water | 71.8 |

The concentration of all components is expressed as percent by weight. The lipid and hydrophilic components are separately warmed and then mixed under shear after which the composition is cooled to room temperature while stirring.

EXAMPLE 4

| | |
|---|---|
| Special Petrolatum Fraction (USP) | 5.0 |
| Octanol | 0.5 |
| Phenylethyl alcohol | 1.0 |
| Cyclomethicone | 9.5 |
| Dimethicone copolyol | 9.5 |
| Sorbitan laurate | 1.0 |
| Water | 73.5 |

The concentration of all components is expressed as percent by weight. The lipid and hydrophilic components are separately warmed and then mixed under shear after which the composition is cooled to room temperature while stirring.

EXAMPLE 5

| | |
|---|---|
| Special Petrolatum Fraction (USP) | 6% |
| Cyclomethicone and Dimethicone copolyol | 9.5% |
| Sorbitan monolaurate | 0.5% |
| Cyclomethicone | 9.2% |
| Benzyl alcohol | 1.0% |
| Ethanol | 3.5% |
| Aqueous solution (0.7% sodium chloride) to | 100% |

The concentration of all components is expressed as percent by weight. The lipid and hydrophobic components are separately warmed and then mixed under shear after which the composition is cooled to room temperature while stirring.

EXAMPLE 6

| | |
|---|---|
| Special Petrolatum Fraction | 0.5% |
| Benzyl Alcohol | 0.5% |
| Jojoba esters | 3.0% |
| Cyclomethicone | 38.0% |
| Liquid Petrolatum | 58.0% |

Dissolve the special petrolatum fraction, benzyl alcohol, jojoba esters in the liquid petrolatum with heat if needed. Cool and add the cyclomethicone. The result is a clear to translucent fluid.

EXAMPLE 7

| | Shampoo | Lotion |
|---|---|---|
| Coal tar | 3% | 3% |
| Sodium laural sulfate | 20% | |
| Polysorbate 80 | 3.0% | 4% |
| Cocamide DEA | 2.0% | 1.0% |
| Glycol | 1.5% | 2.0% |
| Benzyl alcohol | 1.0% | 1.0% |
| Citric Acid | 0.3 to 1% | 0.3% |
| to 1% | | |
| Aluminum Magnesium Silicate | 1.0% | 2.0% |
| Water | Q.S. | Q.S. |

Disperse and hydrate the aluminum magnesium silicate in part of the water. Separately combine, and then add, all of the other ingredients. Add the citric acid last to adjust the pH to the desired value.

It should be understood, of course, that the foregoing relates only to preferred embodiments of the present invention and that numerous modifications or alterations may be made therein without departing from the spirit and the scope of the invention as set forth in the appended claims.

What is claimed is:

1. An ointment base for use on a surface, in which at least 10 percent by weight thereof is composed of an admixture comprising:

a. 2.5 to 90 percent by weight of high molecular weight petrolatum fractions in which the ratio by weight of solid constituents to constituents that are liquid at 20° to 50° C. is greater than 3:1;

b. approximately 4 to 40 percent by weight of a solvent material for the petrolatum fractions; and c. between approximately 0.5% and 10% by weight of a material that is both hydrophobic and hydrophilic.

2. The ointment base of claim 1, wherein the material serving as a solvent is selected from the group consisting of octamethylcyclotetrasiloxane, decamethylcyclopentasiloxane, hexamethyldisiloxane and a mixture thereof.

3. The ointment base of claim 1, wherein the material that is, both hydrophobic and hydrophilic is an aromatic alcohol.

4. The ointment base of claim 3, wherein the aromatic alcohol is selected from the group consisting of benzyl alcohol and phenylethyl alcohol.

5. The ointment base of claim 1, wherein the material that is both hydrophobic and hydrophilic is selected from the group consisting of an aliphatic alcohol with between 7 and 20 carbon atoms and an aliphatic ester with between 7 and 20 carbon atoms.

6. The ointment base of claim 5, wherein the aliphatic alcohol is selected from the group consisting of octanol, and dodecanol.

7. The ointment base of claim 1, wherein the material that is both hydrophobic and hydrophilic is a silanyl compound.

8. The ointment base of claim 7, wherein the silanyl compound is selected from the group consisting of silanyl aldehydes, silanyl esters, and silanyl ketones or mixtures thereof.

9. The ointment base of claim 1, wherein the material that is both hydrophobic and hydrophilic is selected from the group consisting of benzyl glycolate, glyceryl benzoate, phenylethyl alcohol and glyceryl p-amino benzoate.

10. The ointment base of claim 1, wherein the material that is both hydrophobic and hydrophilic is selected from the group consisting of benzophenone and glyceryl p-amino benzoic acid.

11. The ointment base of claim 1, in which the ratio by weight of the petrolatum fractions to the solvent material is in the range from approximately 15:70 to 70:20.

12. The ointment base of claim 1, in which the petrolatum fractions contain substantially no constituents having fewer than 20 carbon atoms per molecule.

13. The ointment base of claim 1, in which the petrolatum fractions contain less than approximately 20 percent by weight of white oils.

14. The ointment base of claim 1, in which the ratio of solid to liquid constituents of the petrolatum fractions is in the range from approximately 4 to 100.

15. The ointment base of claim 14, in which the ratio by weight of the petrolatum fractions to the solvent material is in the range from approximately 80:20 to 80:10.

16. The ointment base of claim 1, in which high melting microcrystalline waxes are included as an additive therein.

17. The ointment base of claim 16, in which the high melting microcrystalline wax additive is present in a proportion of between 3 and 15 percent relative to the combined weight of petrolatum fractions and the solvent material.

18. An ointment base for protecting a surface comprising:

a. approximately 6% by weight of a high molecular weight petroleum fraction;

b. approximately 9% by weight of dimethicone copolyol;

c. approximately 9.5% by weight of cyclomethicone;

d. approximately 0.5% by weight of of sorbate 20;

e. approximately 0.8% by weight of benzyl alcohol;

f. approximately 5% by weight of ethanol; and g. approximately 69.2% by weight of water.

19. A method of protecting a surface comprising the step of applying an ointment base onto the surface, the ointment base comprising a composition in which at least 10 percent by weight thereof is composed of an admixture comprising:

a. 2.5 to 90 percent by weight of high molecular weight petrolatum fractions in which the ratio by weight of solid constituents to constituents that are liquid at 20° to 50° C. is greater than 3:1;

b. approximately 4 to 40 percent by weight of a solvent material for the petrolatum fractions; and c. between approximately 0.5% and 10% by weight of a material that is both hydrophobic and hydrophilic.

20. The method of claim 19, wherein the material serving as a solvent is selected from the group consisting of octamethylcyclotetrasiloxane, decamethylcyclopentasiloxane, hexamethyldisiloxane and a mixture thereof.

21. The method of claim 19, wherein the material that is both hydrophobic and hydrophilic is an aromatic alcohol.

22. The method of claim 21, wherein the aromatic alcohol is selected from the group consisting of phenylethyl alcohol and benzyl alcohol.

23. The method of claim 19, wherein the material that is both hydrophobic and hydrophilic is an aliphatic alcohol with between 7 and 20 carbon atoms and an aliphatic ester with between 7 and 20 carbon atoms.

24. The method of claim 23, wherein the aliphatic alcohol is selected from the group consisting of octanol and dodecanol.

25. The method of claim 19, wherein the material that is both hydrophobic and hydrophilic is a silanyl compound.

26. The method of claim 25, wherein the silanyl compound is selected from the group consisting of silanyl aldehydes, silanyl esters, and silanyl ketones or mixtures thereof.

27. The method of claim 19, wherein the material that is both hydrophobic and hydrophilic is benzyl glycolate and glyceryl benzoate.

28. The method of claim 19, wherein the material that is both hydrophobic and hydrophilic is selected from the group consisting of benzophenone and glyceryl p-amino benzoic acid.

29. The method of claim 19, in which the ratio by weight of the petrolatum fractions to the solvent material is in the range from 15:70 to 70:20.

30. The method of claim 19, in which the petrolatum fractions contain substantially no constituents having fewer than 20 carbon atoms per molecule.

31. The method of claim 19, in which the petrolatum fractions contain less than approximately 20 percent by weight of white oils.

32. The method of claim 19, in which the ratio of solid to liquid constituents of the petrolatum fractions is in the range from approximately 4 to 100.

33. The method of claim 32, in which the ratio by weight of the petrolatum fractions to the solvent material is in the range from approximately 80:20 to 80:10.

34. The method of claim 19, in which high melting microcrystalline waxes are included as an additive therein.

35. The method of claim 34, in which the high melting microcrystalline wax additive is present in a proportion of between 3 and 15 percent relative to the combined weight of petrolatum fractions and the solvent material.

36. The method of claim 19, wherein the surface is skin, hair and nails.

37. The method of claim 19, wherein the surface is wood.

38. The method of claim 19, wherein the surface is leather.

39. A method of protecting a surface comprising the step of applying an ointment base to the surface, the ointment base comprising:
   a. approximately 6% by weight of a high molecular weight petroleum fraction;
   b. approximately 9% by weight of dimethicone copolyol;
   c. approximately 9.5% by weight of cyclomethicone;
   d. approximately 0.5% by weight of of sorbate 20;
   e. approximately 0.8% by weight of benzyl alcohol;
   f. approximately 5% by weight of ethanol; and
   g. approximately 69.2% by weight of water.

40. The method of claim 39, wherein the surface is skin, hair and nails.

41. The method of claim 39, wherein the surface is wood.

42. The method of claim 39, wherein the surface is leather.

* * * * *